United States Patent
Yeates et al.

(10) Patent No.: US 9,573,147 B1
(45) Date of Patent: Feb. 21, 2017

(54) AEROSOLIZING NOZZLE AND METHOD OF OPERATING SUCH AEROSOLIZING NOZZLE

(71) Applicant: KAER BIOTHERAPEUTICS CORPORATION, Escondido, CA (US)

(72) Inventors: Donovan B Yeates, Escondido, CA (US); Xin Heng, McKinney, TX (US)

(73) Assignee: KAER Biotherapeutics Corporation, Escondido, CA (US)

( * ) Notice: Subject to any disclaimer, the term of this patent is extended or adjusted under 35 U.S.C. 154(b) by 0 days.

(21) Appl. No.: 15/130,235

(22) Filed: Apr. 15, 2016

(51) Int. Cl.
| B05B 7/04 | (2006.01) |
| B05B 1/02 | (2006.01) |
| A61M 11/06 | (2006.01) |
| A61M 11/00 | (2006.01) |
| B05B 7/12 | (2006.01) |
| B05B 7/10 | (2006.01) |

(52) U.S. Cl.
CPC ............ B05B 7/0483 (2013.01); A61M 11/001 (2014.02); A61M 11/06 (2013.01); B05B 1/02 (2013.01); B05B 7/0475 (2013.01); B05B 7/10 (2013.01); B05B 7/12 (2013.01)

(58) Field of Classification Search
CPC ...... B05B 7/0441; B05B 7/045; B05B 7/0475; B05B 7/2408; B05B 7/0815; B05B 7/10; B05B 7/12
USPC ...................................................... 239/8, 369
See application file for complete search history.

(56) References Cited

U.S. PATENT DOCUMENTS

| 2,152,767 | A | * | 4/1939 | McKnight | ............. B05B 7/0475 239/300 |
| 4,175,706 | A | * | 11/1979 | Gerstmann | ........... B05B 7/0416 239/414 |
| 5,115,981 | A | * | 5/1992 | Callahan | ............... B05B 7/0416 239/402 |
| 5,152,460 | A | * | 10/1992 | Barty | .................... B05B 7/0081 239/290 |
| 6,174,469 | B1 | | 1/2001 | Gañán-Calvo | |
| 6,866,207 | B2 | * | 3/2005 | Kangas | ................... B05B 7/066 239/290 |

(Continued)

OTHER PUBLICATIONS

Rosell-Llompart, Joan and Gañán-Calvo, Alfonso, Turbulence in pneumatic flow focusing and flow blurring regimes. Physical Review E 77 036321 (2008).

(Continued)

Primary Examiner — Arthur O Hall
Assistant Examiner — Alexander Valvis
(74) Attorney, Agent, or Firm — Schlee IP International, P.C.; Alexander R. Schlee (57) ABSTRACT

A nozzle and a method of generating an aerosol from a fluid and a gas by operating the nozzle. The nozzle has an aerosol exit orifice of a larger diameter and a fluid exit orifice of a smaller diameter aligned on a common central axis. A pressurized gas from a pressurized gas exit in close proximity to the fluid exit orifice intersects a fluid jet exiting from the fluid exit orifice at that acute angle and in a distance from the aerosol exit orifice. The method includes aerosolizing a fluid with a viscosity exceeding 4 cSt delivering an inhalable medication at a rate of more than 1 ml/minute, thereby delivering a medication at a mass flow rate of at least 30 mg/minute in form of the fluid particles having a mass median aerodynamic diameter (MMAD) of 6 μm or less.

15 Claims, 6 Drawing Sheets

(56) References Cited

U.S. PATENT DOCUMENTS

| | | |
|---|---|---|
| 7,201,167 B2 | 4/2007 | Fink |
| 8,297,529 B2 * | 10/2012 | Smith ................. B05B 7/08 239/11 |
| 8,739,777 B2 | 6/2014 | Kreutzmann |
| 9,120,109 B2 | 9/2015 | Gañán-Calvo |
| 2005/0196345 A1 | 9/2005 | Diederichs |
| 2009/0217947 A1 * | 9/2009 | Wiederin ............. B05B 7/063 134/18 |

OTHER PUBLICATIONS

Gañán-Calvo, Alfonso M, Enhanced liquid atomization: From flow-focusing to flow-blurring. Applied Physics Letters, 86, 214101 (2005).

Gemci T, and Chigier N, Atomization, spraying and nebulization 201-256, Production Handling and Characterization of Particulate Materials; Henk G Merkus and Gabriel M.H. Meesters, Editors; Springer 2016.

Gañán-Calvo, Alfonso M., Montanero, José M., Revision of capillary cone-jet physics: Electrospray and flow focusing. Physical Review E 79, 066305 (2009).

Walther, Frans J., Hernandez-Juviel, José M., Waring Alan J., Aerosol delivery of synthetic lung surfactant, PeerJ 2:e403; DOI 10.7717/peerj.403 (2014).

Pillow, J. Jane, Miniocchieri, S., Innovation in Surfactant Therapy II: Surfactant Administration by Aerosolization; Neonatology, 2012; 101:337-344.

Finer, Neil N., Merritt, Allen, Bernstein, Graham, Job, Leela, Mazela, Jan, and Segal, Robert. An Open Label, Pilot Study of Aerosurf® Combined with nCPAP to Prevent RDS in Preterm Neonates, Journal of Aerosol Medicine and Pulmonary Drug Delivery vol. 23:1-7 (2010).

Zambon, Massimo, Vincent, Jean-Louis, Mortality Rates for Patients with Acute Lung Injury/ARDS Have Decreased Over Time, Chest 133(5):1120-7 (2008).

Gañán-Calvo, Alfonso M., Generation of Steady Liquid Microthreads and Micron-Sized Monodisperse Sprays in Gas Streams, Physical Review Letters, vol. 80, No. 2 (1998).

* cited by examiner

AEROSOLIZING NOZZLE AND METHOD OF OPERATING SUCH AEROSOLIZING NOZZLE

GOVERNMENT SUPPORT

The present invention, in part, was supported by the National Institutes of Health, Heart, Lung and Blood Institute under grant R43HL127834. The U.S.Exzampl government has certain rights to this invention.

BACKGROUND OF THE INVENTION

The generation of high concentrations of fine particle respirable aerosols from viscous solutions and solutions containing solutes of high molecular weight compounds and or liposomes have been fraught with difficulty, especially if these solutions have low surface tensions. Deep lung deposition is best achieved by inhaling particles having a mass median aerodynamic diameter (MMAD) of less than 4 μm. The present disclosure relates to a nozzle for creating liquid aerosols from solutions or suspensions including those of high viscosity and low surface tension together with the evaporation of the liquid from these aerosols to further reduce the particle size and to markedly increase the particle concentration in the suspending gas while reducing the total gas output to be more in balance with a desired delivery rate for particle collection, as well as their delivery to animals and humans.

Acute respiratory distress syndrome, ARDS, including acute lung injury, ALI, are of multifactorial etiology and afflict 190,000 Americans each year including 18% of all ventilated patients. Despite sophisticated intensive care, the mortality rate ranges between 15 and 72% with a mean of 43%. Patients with ARDS have impaired surfactant function and continued inflammation-induced inactivation of surfactant indicating that a single treatment with surfactant is likely inadequate. Surfactant delivery to patients with ARDS demonstrates that instillation of surfactant may improve oxygenation for ≥120 hours. However liquid bolus administration of surfactant results in a high rate of adverse effects and thus cannot be considered an effective adjunctive therapy in patients with acute lung injury. Multiple boluses of intrapulmonary instillations of surfactant are traumatic for the patient and physician alike and lead to undesirable peri- and post-treatment events. The delivery of surfactant in a gentler, non-invasive manner would empower physicians to provide improved life support and potentially a marked improvement in survival.

In the following, various prior art options for aerosol surfactant delivery are discussed. The delivery of pulmonary surfactant to treat lung diseases such as ARDS and respiratory distress syndrome, RDS, has been via the instillation of 20 to 80 mg/ml of suspensions of surfactant at doses generally ranging from 100 mg to 200 mg/kg or 100-700 ml for a 70 kg adult. Aerosolized surfactant may require a considerably lower dose (1/20) to achieve a similar physiological effect. It also eliminates the hypercapnia seen on bolus instillation. However, it is not yet part of the clinical armamentarium. This has been largely due to the difficulty of aerosolizing and delivering high concentrations of surfactant within a relatively short treatment time. In neonates, aerosolized surfactant was delivered over 3 hours. This situation is markedly exacerbated when attempting to deliver the same dose/kg of aerosolized surfactant to adults.

Mesh-type nebulizers generate soft mists through the creation of aerosols formed by liquids passing through an array of 2-3 μm diameter holes in a mesh. The energy to produce the aerosol is provided by electromechanical vibration of the mesh, or a horn located behind the mesh. A major drawback, however, is that the output of these nebulizers is limited by the viscosity of the nebulized formulation. Using low molecular weight polyols, it was demonstrated that the output markedly decreased or ceased when the viscosity was greater than 2 cSt (~2 cSt). The output of surfactant from one such nebulizer known by the trade name Aeroneb has been reported to aerosolize 0.1 ml/min resulting in the delivery of just 3 mg/min of surfactant at its output.

While jet type atomizers can aerosolize more viscous solutions their output is generally reduced to about 0.3 ml/minute or less for particles sizes of about 3 μm mass median aerodynamic diameter, MMAD. Aerosol outputs of surfactant of up to 7 mg/min have been reported by using these jet type atomizers. In addition, jet type atomizers typically recirculate the fluid that is not presented at the output leading to increasing concentrations of the solute, sol or liposomal content resulting in increased viscosity, decreased output and a change in the particle size. In addition, foam created in by surface active agents in the atomizer can also dramatically inhibit aerosol formation.

A capillary aerosol generator has been reported to be used by Discovery Laboratories to deliver surfactant to neonates. In this generator the surfactant suspension is heated in a capillary tube and evaporated. The output aerosol comprises the particles condensed on nuclei when the vapor is cooled. Such devices have the potential to cause heat-induced surfactant degradation. This device can take over an hour to produce 100 mg of surfactant in aerosol form.

Recently surfactant has been reported to be delivered from dispersing a dry powder of surfactant. Delivery rates of 6.6 mg/min in 0.84 liters of air have been reported. However, the efficiency of the delivery system has not been reported and is considered likely very low.

From the U.S. Pat. No. 9,120,109 B2 aerosol generation from a nozzle is known comprising a fluid supply through a fluid supply orifice in close proximity to a plate, with the plate having an orifice of the same size as the fluid supply orifice. This proximity of the fluid supply orifice to the plate orifice was 0.1 to 0.25 times the diameter of these orifices. This patent further describes a transition from focused-flow (FF) to turbulent-flow-focusing (TFF) to flow-blurring (FB) and describes an observed reduction in particle size as the Reynolds number increases to what is likely a fully developed turbulent flow.

The aforementioned prior art technologies have not been shown to provide clinically relevant doses of surfactant to the adult respiratory tract, let alone to deliver a high mass in a short treatment time targeted at alveolar deposition. Therefore, these prior art technologies fall short on delivering certain drugs at the required delivery rate, for instance to treat ARDS and other respiratory diseases whose efficacy may depend on higher doses being delivered to the lungs in a shorter time span.

SUMMARY OF THE INVENTION

It is an object of the invention to create a nozzle and a corresponding method of operating such a nozzle that enables efficient generation of an aerosol comprising small particles from fluids, including those of relatively high viscosities, and/or with low surface tensions, at a high aerosolization rates with a relatively narrow particle size distributions.

It is another object of the invention to avoid any formation of larger droplets dripping from an outer surface of the nozzle, specifically when aerosolizing fluids of higher viscosity and at a high aerosolization rate.

Additional objects of the invention become apparent from the advantages achieved and described below.

These and other objects are achieved by a nozzle for generating from a fluid and a gas an aerosol comprising fluid particles, the nozzle comprising an aerosol exit orifice extending to an outer nozzle surface, wherein the aerosol exit orifice has an aerosol exit orifice diameter, a central axis and has a circumferential edge from which an aerosol exit channel extends from the outer nozzle surface toward an aerosolizing space within the nozzle. The nozzle further comprises a fluid exit orifice that is aligned on the same central axis as the aerosol exit orifice and opens into the aerosolizing space within the nozzle at a distance from an entrance to the aerosol exit channel, the aerosol exit orifice diameter being at least 1.3 times larger than the fluid exit orifice diameter. At least one converging annular pressurized gas channel extends at an acute flow angle with respect to the central axis and has a pressurized gas exit in close proximity to the fluid exit orifice so as to intersect with fluid exiting from the fluid exit orifice.

The corresponding method for operating this aforementioned nozzle according to the incident invention comprises aerosolizing a fluid with a viscosity exceeding 4 cSt delivering an inhalable medication; and aerosolizing the fluid at a rate of more than 1 ml/minute, thereby delivering a medication at a mass flow rate of at least 30 mg/minute in form of the fluid particles having a mass median aerodynamic diameter (MMAD) of 6 µm or less.

DETAILED DESCRIPTION OF THE INVENTION

According to a preferred embodiment, an aerosol exit orifice extends to an outer nozzle surface, wherein the aerosol exit orifice has an aerosol exit orifice diameter, a central axis and has a circumferential edge from which an aerosol exit channel extends from the outer nozzle surface toward an aerosolizing space within the nozzle, an aerosol exit channel length of the aerosol exit channel being less than the aerosol exit orifice diameter. There is an aerosolizing space within the nozzle. To supply fluid to be aerosolized within the aerosolizing space, a fluid exit orifice aligned on the same central axis as the aerosol exit orifice opens into the aerosolizing space within the nozzle at a distance from the entrance to the aerosol exit channel. The diameter of the fluid exit orifice is smaller than the aerosol exit orifice diameter. At least one, but preferably two or more circumferentially spaced pressurized gas supply channels lead to a pressure equalization chamber, and a circumferential converging annular channel at an acute angle with respect to the central axis that has a pressurized gas exit opening in close proximity to the fluid exit orifice so that at least a central portion of this pressurized gas interacts with fluid exiting from the fluid exit orifice and a peripheral portion of this gas exits the aerosol exit orifice without substantial interaction with the liquid, especially when the aerosol exit diameter is 1.5 times larger than the diameter of the fluid exit orifice. Of note, the configuration of this preferred embodiment is designed for maintaining the patency of the converging annular pressurized gas channel by the elimination of "dead volumes" wherein fluid may accumulate and potentially result in nozzle malfunction.

Preferably, an aerosol exit channel length of the aerosol exit channel is less than the aerosol exit orifice diameter. A comparatively short aerosol exit channel facilitates the use of the nozzle over a wide range of pressurized gas, especially those pressures above 103 kPa (15 psi) and also minimizes the collection of any fluid particles on the exit channel.

As a particularly surprising effect of the incident invention, the aerosol formed within the nozzle exits through an aerosol exit orifice within a central core surrounded by a sheath of gas largely, if not entirely, devoid on particles. This sheath helps prevent droplets depositing on the outer surface of the nozzle that may cause the dripping of fluid.

The fluid to be aerosolized, may be a medication having a fluid viscosity which may be as high as 100 cSt and that may be aerosolized even at rates between 100 µl and 3 ml/minute, thereby delivering masses of a medication from 30 to 285 mg/minute with a fluid particle size having a mass median aerodynamic diameter (MMAD) of 6 µm or less.

The invention enables the generation of fine particle aerosols from solutions with viscosities up to at least 40 cSt with a relatively narrow size distribution ($\sigma_g$ of less than 2.4 and in many cases less than 2). Another advantage of the incident invention is that the liquid aerosol is prevented from contacting the gas confining aerosol exit orifice, as the liquid aerosols are generated with a gas sheath between the stream of aerosol generated and the perimeter of the aerosol exit nozzle. This results in a generation of aerosols by a single pass nozzle with 100% aerosol generation efficiency. Consistent with this 100% aerosol generation efficiency, aerosols can be generated over a period of at least 8 hours without substantial solute build-up on the nozzle.

The incident invention further accomplishes generating fine particle aerosols with relatively low pressures from solutions, and solutions of liposomes and sols.

By combining the incident invention with additional device elements, the particle size can be further reduced by the evaporation of the solvent from the aerosols generated by the nozzle through dilution of the droplet aerosol with a dilution gas followed by increasing the particle concentration of these aerosols using a virtual impactor. This results in a smaller diameter dry powder aerosol in a reduced gas volume.

The incident invention further accomplishes delivering these aerosols at flow rates between 10 l/min to 200 l/min and delivering fine particles aerosols of surface active agents at rates of over 100 mg/min.

According to an embodiment of the invention, in this nozzle for generating fine particles aerosols from a solution or suspension, a fluid to be aerosolized is fed by means of a pump through a channel of length 1.5 mm and 250 µm in diameter within a first cone-like structure having an acute conical wall angle of 17 degrees from its axis and tapered towards the output of the channel contained therein, hereinafter referred to as a fluid exit orifice. Coaxial with this channel is an aerosol exit orifice that is larger than that of the fluid exit orifice and in a preferred configuration separated by a distance of 0.5 mm from the entrance to an aerosol exit channel. In a preferred arrangement, the diameter of the aerosol exit orifice is between 1.5 and 4 times larger than the diameter of the fluid exit orifice and hereinafter referred to as an aerosol exit orifice. At its circumference, in a preferred configuration, the aerosol exit channel length through which this aerosol exit orifice penetrates is just 180 µm. An external surface surrounding this aerosol exit orifice is of convex parabolic nature such that eddies in the gas flow around the aerosol exit orifice are minimized as is any particle deposition on or near this aerosol exit orifice. A pressurized gas exit is coaxially centered in a second cone-like structure at the apex of which is the aerosol exit channel. Preferably, the converging annular pressurized gas channel comprises a first partial annular channel and a second partial annular channel, the first partial annular channel has inner and outer walls formed by a conical wall and an inner front insert wall along which the pressurized gas flows with the acute flow angle being determined by a conical wall angle and a front insert wall angle with respect to the central axis in the area of the fluid exit orifice. The circumferential walls of this second cone-like structure leading to this pressurized gas exit encloses preferably an acute angle of 35 degrees adjacent to the nozzle, i.e. the angle between the central axis and the circumferential cone surface is about 17.5 degrees, such that there is a circumferential converging gas channel between the inner first cone-like structure and the second cone-like structure.

According to a preferred embodiment, the fluid supply channel is provided within a cone-shaped fluid supply nozzle insert forming the conical wall that is the inner wall of the first partial annular channel, designed as a converging circumferential compressed gas channel that is axially centered in a cone shaped hollow space of the front insert forming the inner front insert wall that is the outer wall of the first partial annular channel.

Compressed gas enters two ports in a nozzle holder barrel and in a preferred configuration flows through two 1.2 mm diameter channels along the nozzle holder barrel. The channels terminate in a small annular chamber which enables equalization of the gas pressure and thus uniform flow of this gas between the fluid cone and the second cone-like structure such that the central portion of the gas interacts with the fluid as it exits from the fluid exit orifice. This fluid is aerosolized within the aerosolizing space between the fluid exit orifice and the entrance to the aerosol exit channel so that the aerosol exits the aerosol exit orifice as a column-like stream of aerosol particles surrounded by a sheath of gas at the aerosol exit orifice that is devoid of particles. An exterior surface of the exit orifice is convex to prevent eddies and particle deposition surrounding the aerosol exit orifice.

According to a preferred embodiment for generating a dry powder aerosol, this column of aerosol particles enters an evaporation chamber. A coaxial counter-flow jet of gas arrests the plume about half-way between a counter-flow output port and the aerosol exit orifice. This aerosol is transported along a quartz evaporation chamber by a dilution gas to a virtual impactor. The compressed gas for the nozzle and counter-flow gas as well as the dilution gas can be heated to enhance the evaporation of the fluid from the particles. In addition, to enhance evaporation of the fluid for the aerosol droplets there is an infrared bulb located adjacent to the evaporation chamber and an infrared reflector on the opposite side of the evaporation chamber. The evaporation chamber is comprised of a quartz tube as quartz is transparent to infrared radiation. The rate and degree of fluid evaporation is controlled by the temperatures and flow-rates of the gasses as well as the intensity of the infrared radiation. The resultant aerosol is accelerated by acceleration nozzles in the virtual impactor. The momentum imparted to these particles carries them across a small gap where most of the gas escapes the aerosol mutually perpendicular to the gas flow and most of the aerosol particles enter aligned deceleration nozzles on the other side of the gap. The aerosol exiting the deceleration nozzles flows through an output cone.

According to a preferred embodiment, the aerosol exit orifice diameter is at least 1.5 times larger than the fluid exit orifice diameter. Other variations are possible, for instance aerosol exit orifice diameter may be 1.3-5 times larger than the fluid exit orifice diameter.

According to another preferred embodiment, the distance between the fluid exit orifice and the entrance to the aerosol exit channel defining a length of the aerosolizing space is between 50 µm and 2 mm. More particularly, the length of the aerosolizing space may be between 200 µm and 1 mm. The aerosol is formed within the aerosolizing space that is provided within the nozzle, i.e. the aerosol forms substantially within the nozzle. As a more particular example, a length of the aerosolizing space of 500 µm has proven to be effective.

According to another preferred embodiment, at least 2 pressurized gas supply channels are circumferentially spaced with respect to each other and extend to a pressure equalization chamber. It is possible to have more than two circumferentially spaced pressurized gas supply channels, for instance 6 or more around the circumference, depending on how much space is available for accommodating circumferentially spaced pressurized gas supply channels of sufficient cross-section.

In a preferred embodiment the nozzle comprises a barrel holding the cone-shaped fluid supply insert which incorporates the fluid exit orifice. The front insert forms the outer nozzle surface, and at least part of the cone shaped hollow space forms the outer wall of the first partial annular channel of the at least one converging annular pressurized gas channel. This design has the converging annular channel that has cone-shaped inner and outer walls. This design is manufacturing and assembly friendly and provides a good sized cross-section of the converging annular channel that can be easily adjusted by adjusting the inner diameter of the cone shaped hollow space of the front insert and/or the outer diameter of the cone-shaped fluid supply nozzle insert. This way, a preferable divergence of the first partial annular channel, for instance at an acute divergence angle between 1 and 30°, can be established, the acute divergence angle being the difference between the conical wall angle and the front insert wall angle. This divergence helps prevent a back flow of the fluid, specifically when the front insert wall and the conical wall are made hydrophobic, omniphobic or lyophobic.

According to another preferred embodiment, the outer nozzle surface area is convex in the area of the aerosol exit orifice. Specifically, it is preferred if the aerosol exit orifice has a substantially sharp edge with respect to the outer nozzle surface through which the aerosol exit orifice opens. Further, it is preferred if at least the outer nozzle surface area around the aerosol exit orifice is not recessed, i.e. the aerosol exit orifice is not provided within a dimple in the outer nozzle surface. A comparatively short aerosol exit channel length helps to enable higher aerosol exit orifice gas flows and avoids any accumulation of droplets or solid material around the aerosol exit orifice and any ensuing dripping.

Preferably, the aerosolizing space has the shape of a truncated cone having its small diameter at an entrance to the aerosol exit channel. The aerosol exit channel is very short, for instance substantially shorter than the diameter of the aerosol exit orifice.

Preferably, the inner and outer walls and the outer nozzle surface area are hydrophobic, omniphobic, or lyophobic.

According to a preferred embodiment, the aerosol exit orifice has a diameter between 400 µm and 1.2 mm. A goal is to avoid a focused flow with a Raleigh breakup in the cone-shaped plume at a distance from the aerosol exit orifice, but rather, according to the invention, to create a more column shaped aerosol plume that is essentially formed already within the nozzle in the aerosolizing space. Specifically, diameters between 500 µm and 1 mm have turned out to be advantageous, but any diameter works that is large enough to avoid the focused flow as known in the prior art but at the same time defines an aerosolizing space within the nozzle so that the aerosol is predominantly formed within the nozzle and exits as an aerosol through the aerosol exit orifice.

According to a preferred embodiment, the acute angle is between 10 and 60°. Specifically advantageous is an angle of between 10 and 45°, more preferably between 13 and 30°. Additionally, the pressure impeding fluid flow between two converging lyophobic surfaces at an acute angle must increase as the surfaces approach each other. Thus, in the nozzle this impedes or prevents fluid back flow in the converging annular pressurized gas channel to the pressure equalization chamber and reduces or eliminates any resultant untoward effects on the aerosolization mechanisms.

According to a preferred embodiment of the method of operating the nozzle, an additional method step is forming the aerosol within the aerosolizing space and exiting this aerosolizing space by the aerosol within a sheath of gas largely devoid of any aerosol particles. This also refers to the preferred column shaped plume with the particle-free sheath around the plume at the aerosol exit orifice avoiding particles impacting with a nozzle surface and accumulating or dripping from that surface.

According to another preferred embodiment of the method, the method comprises the method of generating the aerosol particles having a particle size at a given gas pressure that is smaller than generating these particles from a smaller orifice under conditions of focused flow.

Preferably, the size of the particles generated is substantially inviscid for fluid viscosities less than 40 cSt, i.e. the influence of the viscosity on the particle size is independent from the viscosity—apart from a minor influence that may for many practical purposes be ignored.

In a preferred embodiment, the fluid to be aerosolized is a surfactant suspension, particularly for the treatment of ARDS as high surfactant delivery rates are required.

According to a preferred embodiment, the method further comprises the method step of drying the particles by evaporating fluid from the aerosol particles and increasing their concentration using a virtual impactor to generate smaller dry powder particles in a reduced volume.

According to a preferred embodiment, the fluid to be aerosolized is a surfactant suspension that mimics lung surfactant.

According to a preferred embodiment, the method further comprises a step of drying the particles by evaporating fluid from the aerosol particles and increasing their concentration using a virtual impactor to generate smaller dry powder particles in a reduced volume.

According to a preferred embodiment, the method further comprises generating fine particle aerosols from solutions with viscosities greater than 40 cSt.

According to a preferred embodiment, the method further comprises generating fine particle aerosols from aqueous suspensions with low surface tensions.

According to a preferred embodiment, the method further comprises choosing the acute flow angle between 13 and 30°.

According to a preferred embodiment, the method further comprises providing the surfaces of the converging annular channel and pressure equalization chamber with hydrophobic, omniphobic or lyophobic properties to avoid wetting of these surfaces by solution or suspension residues.

According to a preferred embodiment, the method comprises impeding or preventing back flow of the aerosolizing fluid and potential nozzle malfunction by choosing an appropriate acute divergence angle and by making the inner front insert wall and the conical wall of the first partial annular channel hydrophobic, omniphobic or lyophobic.

DETAILED DESCRIPTION OF THE DRAWINGS

Figure 1:
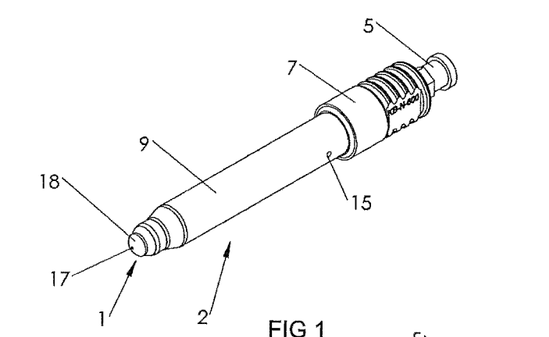
FIG. 1 shows a perspective view of an embodiment of a nozzle according to the invention assembled to a nozzle holder.
Figure 2:
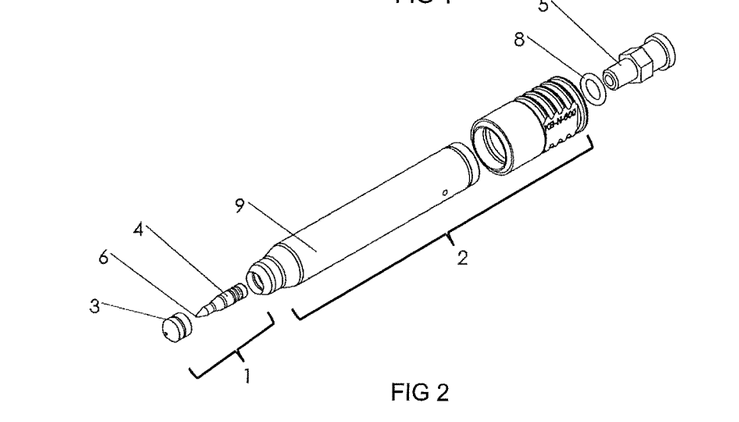
FIG. 2 shows an exploded perspective view of the nozzle and nozzle holder shown in FIG. 1.
Figure 3:
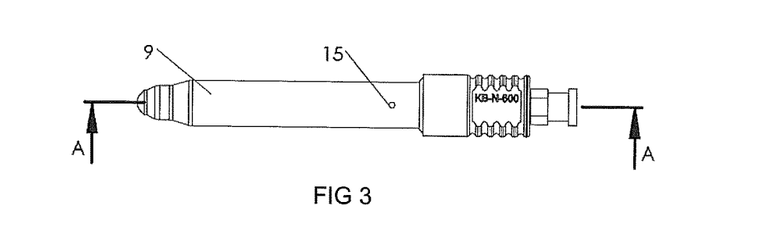
FIG. 3 shows a side view of the nozzle and nozzle holder shown in FIG. 1.
Figure 4:
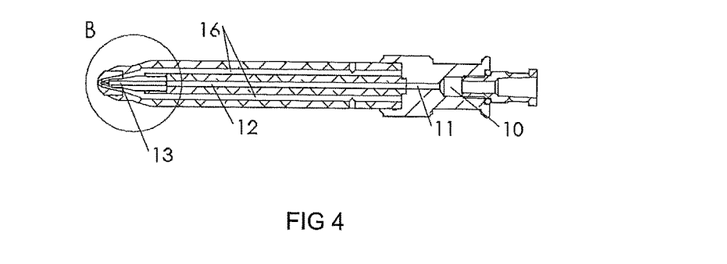
FIG. 4 shows a sectional view of the nozzle and nozzle holder along the plane A-A as indicated in FIG. 3.

Referring to FIGS. 1-9 a nozzle 1 according to the incident invention that is mounted to a nozzle holder 2 is shown. In a preferred configuration these parts are made of ULTEM™ resin, albeit other materials may be used. As best seen in FIG. 2, the nozzle 1 includes a front insert 3 and a cone-shaped fluid supply nozzle insert 4. A fluid to be aerosolized is fed under pressure into a Luer connector 5 that is connected to a knob 7 on the nozzle holder 2. At the front end of the nozzle 1, specifically according to this embodiment in the front insert 3, the nozzle 1 comprises an aerosol exit orifice 17 located at an outer nozzle surface 18 having a circumferential edge 19 (see FIG. 7). There is an aerosolizing space 20 between a fluid exit orifice 6 (see FIGS. 5 and 9) and an entrance 53 to an aerosol exit channel 49 and bounded by an aerosolizing space wall 62 (see FIGS. 5 and 7). The aerosol exit orifice 17 has an aerosol exit orifice diameter 21 and a central axis 22.

Figure 5:
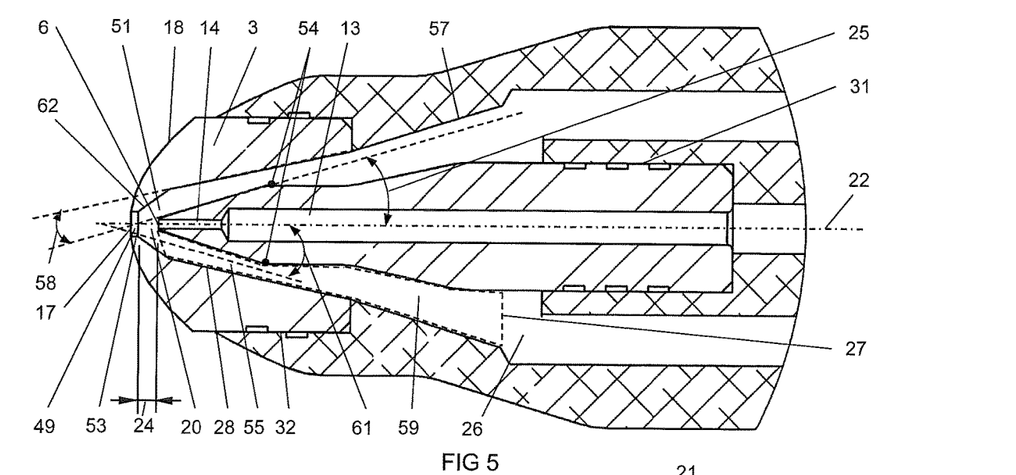
FIG. 5 shows a detail sectional view of the nozzle and nozzle holder of the detail B as indicated FIG. 4.
Figure 6:
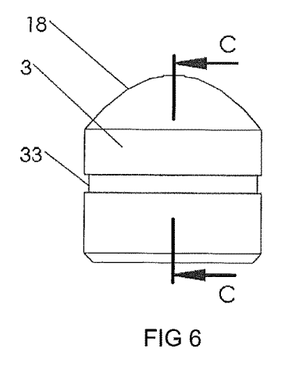
FIG. 6 shows a side view of a front insert of the aerosol exit nozzle shown in FIGS. 1-5.
Figure 9:
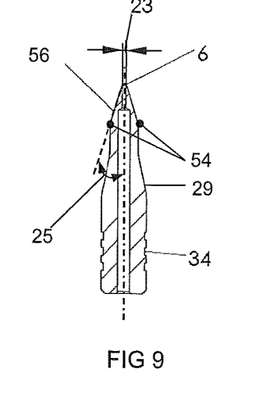
FIG. 9 shows a sectional view of the cone-shaped fluid supply nozzle insert along the plane E-E as indicated in FIG. 8.

As the fluid is fed under pressure through the Luer connector 5, an O-ring 8 prevents any fluid leakage between the Luer connector 5 and the knob 7. The nozzle holder 2 includes a barrel 9 such that the fluid, in a preferred configuration, flows through the Luer connector 5 to channel 10 and from there through channel 11 to channel 12 within the barrel 9 of the nozzle holder 2. This fluid then flows from channel 12 to channel 13 and into a very narrow fluid supply channel 14 that in a preferred configuration is 250 μm in diameter and 1.5 mm long but other diameters between 20 and 400 μm are also feasible options. At the end of the very narrow fluid supply channel 14 the fluid exit orifice 6 is provided, and having, according to this embodiment, the same fluid exit orifice diameter 23 as the very narrow channel 14.

Compressed gas enters the barrel 9 of the nozzle holder 2 through gas entry ports 15 on each side of the barrel 9. This gas flows into each of two pressurized gas supply channels 16 towards (see FIG. 4) the nozzle 1. According to one embodiment, the pressurized gas supply channel 16 leads to a pressure equalization chamber 26 and a converging annular pressurized gas channel 27 converging to an annular neck 54. The converging annular pressurized gas channel 27 comprises a first partial annular channel 55 extending between the annular neck 54 and the fluid exit orifice 6, while a second partial annular channel 59 extends substantially between the annular neck 54 and the pressure equalization chamber 26. Due to the annular neck 54, the second partial annular channel 59 also acts to uniform gas flow to the first partial annular channel 55. In the first partial annular channel 55 an inner front insert wall 28 and a conical wall 56 are diverging, at an acute divergence angle 58, from which the gas enters into the aerosolizing space 20 in the proximity of fluid orifice exit 6. The average between the conical wall angle 25 and the front insert wall angle 60 determined by the sum of the conical wall angle 25 and the front insert wall angle 60 divided by two and is hereinafter referred to in case of divergence simply as the acute gas flow angle 61 like in case of a non-diverging first partial annular channel 55.

The converging annular pressurized gas channel 27 is defined by the inner front insert wall 28 together with a converging wall 57 in the barrel 9 and an outer cone-shaped fluid supply nozzle insert wall 29. The first partial annular channel 55 is defined by the inner front insert wall 28 and conical wall 56 adjacent to the fluid exit orifice 6 extending at an acute conical wall angle 25 with respect to the central axis 22. Several of the pressurized gas supply channels 16 can be provided in a circumferentially spaced fashion with respect to each other, leading to the pressure equalization chamber 26, and the converging annular pressurized gas channel 27. Beneficial from a manufacturing and assembly point of view is an embodiment with the front insert 3 and cone-shaped fluid supply nozzle insert 4, the respective component parts being shown in FIGS. 6-9, where for the purpose of assembly, the barrel 9 of the nozzle holder 2 is provided with a first hole 31 into which the cone-shaped fluid supply nozzle insert 4 is inserted, and a second hole 32 into which the front insert 3 is inserted. By choosing appropriate tolerances for the holes 31 and 32 in relation to the outer diameters of the inserts 4 and 3, respectively, these may hold themselves in place by frictional forces. A more economic manufacturing method can be accomplished by gluing the inserts 3 and 4 into the respective corresponding holes 32 and 31, and for accommodating glue, respective recesses 33 and 34 can be provided in the respective inserts 3 and 4, as shown in FIGS. 6-9.

Figure 7:
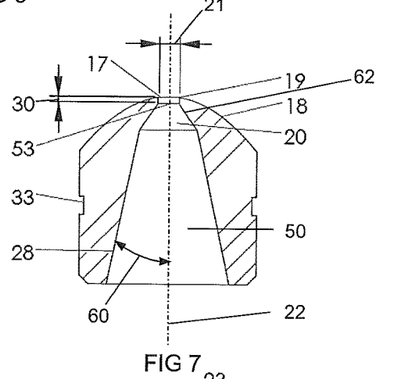
FIG. 7 shows a sectional view of the front insert along the plane C-C as indicated in FIG. 6.
Figure 8:
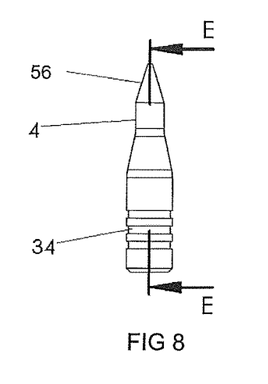
FIG. 8 shows a side view of a cone-shaped fluid supply nozzle insert of the nozzle shown in FIGS. 1-5.

According to this embodiment, the gas flows from the pressurized gas supply channels 16 into the pressure equalization chamber 26 and from there into the converging annular pressurized gas channel 27 and into the first partial annular channel 55. At a distance 24 from the entrance 53 of the aerosol exit channel 49, the first partial annular channel 55 intersects the central axis 22 in the vicinity of the fluid exit orifice 6. A fluid jet exits through the fluid exit orifice 6 in direction of the central axis 22 where it interacts with the pressurized gas at a pressurized gas exit 51. According to a preferred embodiment, the distance 24 is 500 μm which distance marks approximately the length of the aerosolizing space 20. Other distances between 50 μm and 2 mm are possible. This exiting pressurized gas blasts the fluid exiting the fluid exit orifice 6 at the end of a fluid supply channel 14. As shown in FIG. 7, an aerosol exit channel length 30 within the front insert 3 is preferably small, for instance, according to a preferred embodiment, is just 180 μm. Fine particles are created as a result of this blast of high pressure air exit through the aerosolizing space 20 and the aerosol exit orifice 17 to form an aerosol plume. The fine particles exit through a central core of the aerosol exit orifice 17 to form a column-like aerosol plume. Between the central aerosol core and the circumferential edge 19 of the aerosol exit orifice 17, a concentric particle free zone exists. The high velocity at which the aerosol and therefore the high velocity aerosol gas exits the aerosol exit orifice 17 generates a Venturi effect, entraining particle free gas sweeping over the outer nozzle surface 18. In addition to the concentric particle free zone, the gas entrainment induced by the Venturi effect helps ensure that this outer nozzle surface 18 remains free of particle deposition. Helping with this gas entrainment is the convex shape of the outer nozzle surface 18, preferably an aerodynamically optimized parabolic shape to increase a sweeping effect. These gas channels and chambers 16, 26, 27, 49 as well as the convex outer nozzle surface 18 can be treated to be hydrophobic, omniphobic or lyophobic as a further precaution to maintain nozzle patency and function.

The nozzle according to the invention creates fluid particles (droplets) small enough to be directly inhaled for certain applications. However, a dry powder aerosol might be preferred. The incorporation of these nozzles according to the incident invention in an aerosol processing system shown in FIG. 10 facilitates the evaporation of solvents containing the medication, the reduction of the particle size and enables an increase in the concentration of the number of particles. This dry powder aerosol generating apparatus and several components thereof are described in the U.S. Pat. Nos. 8,596,268; 8,616,532; 8,375,987, these three patents herewith incorporated by reference.

Figure 10:
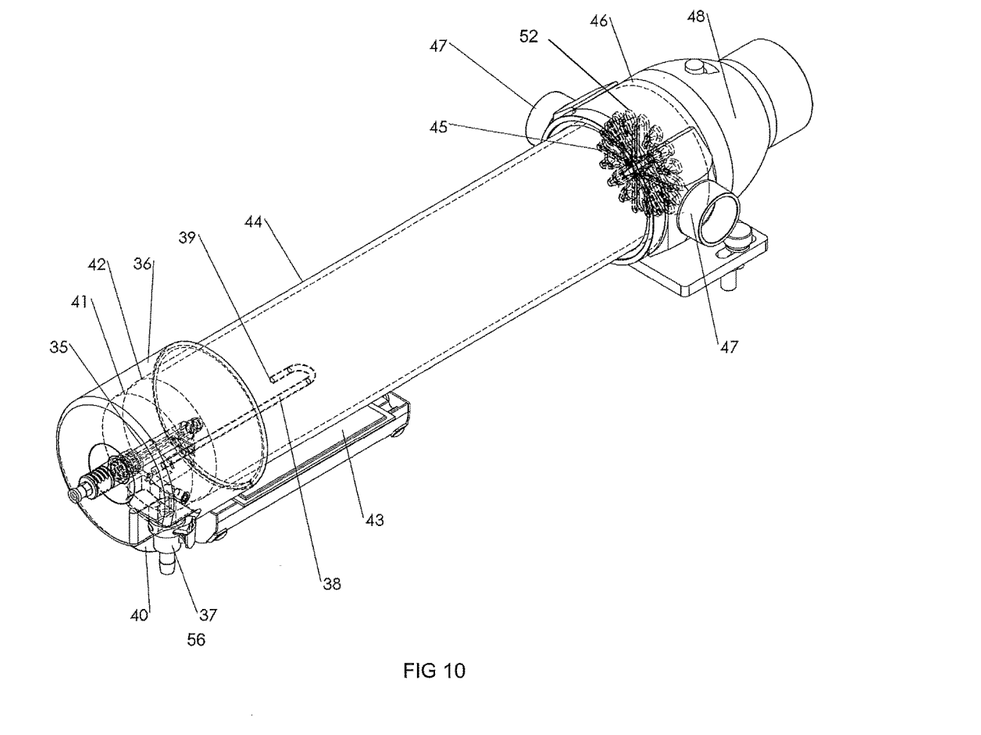
FIG. 10 shows the nozzle and nozzle holder placed in a flow distributer and an aerosol processing system used in conjunction with the nozzle according to the nozzle shown in FIGS. 1-5.

In this arrangement, during operation, the barrel 9 of nozzle holder 2 is inserted into a channel 35 in a flow distributer 36. Compressed gas enters port 37. Within the flow distributer 36, the compressed gas is split into two streams. The first gas flow enters a circumferential grove whose position coincides with the location of the gas entry ports 15 on the barrel 9 of the nozzle holder 2. The second gas flow is constrained by an orifice within the flow distributer 36. The second gas flow flows into a counter-flow tube 38. The orifice diameter in this second flow path is adjusted such that the counter-flow gas arrests the aerosol plume roughly midway between the aerosol exit orifice 17 and an output port 39 of the counter-flow tube 38. The fluid is evaporated from the aerosol particles by the provision of heated gas to both the gas entry ports 15 and the counter-flow tube 38. In addition, a third flow of warmed gas enters port 40 which is conditioned between two baffles 41 and 42. This gas then surrounds the nozzle barrel 9 and dilutes the aerosol emitted from aerosol exit orifice 17. Evaporation is aided by infrared radiation from an infrared source 43. The aerosol transits through a quartz evaporation tube 44 and enters acceleration nozzles 45 on a virtual impactor 46. Most of the gas exits through two exhaust ports 47. Most of the particles cross a gap between the acceleration nozzles 45 and radially aligned deceleration nozzles 52. The concentrated aerosol exits the virtual impactor 46 into an output cone 48.

EXAMPLES

Figure 11A:
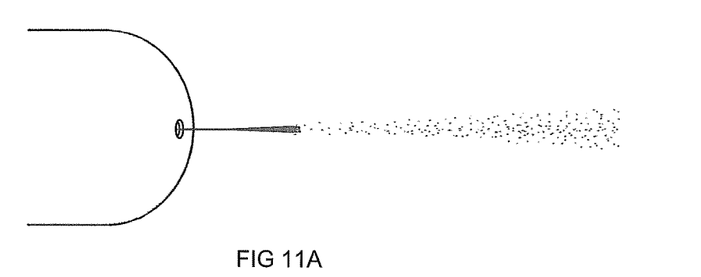
FIGS. 11A-11B shows that the aerosol plume from a nozzle with an aerosol exit orifice of 300 µm in diameter comprises a central fluid stream that breaks into droplets outside of the nozzle at compressed air pressures of both 207 KPa (30 psi) (FIG. 11A) and 414 KPa (60 psi) (FIG. 11B).
Figure 11B:
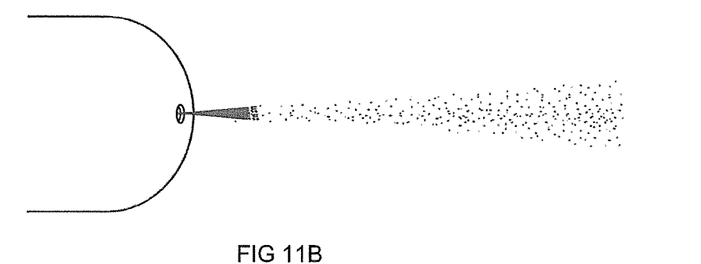
Figure 12A:
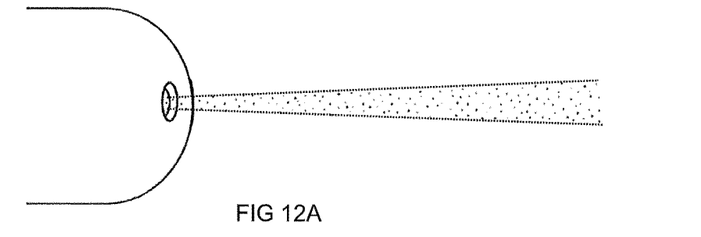
FIGS. 12A-12B shows that the aerosol plume from a nozzle with an aerosol exit orifice of 700 µm in diameter shows that the fluid is aerosolized within the nozzle and forms a columnar like aerosol plume at compressed air pressures of both 207 KPa (30 psi) (FIG. 12A) and 414 KPa (60 psi) (FIG. 12B).
Figure 12B:
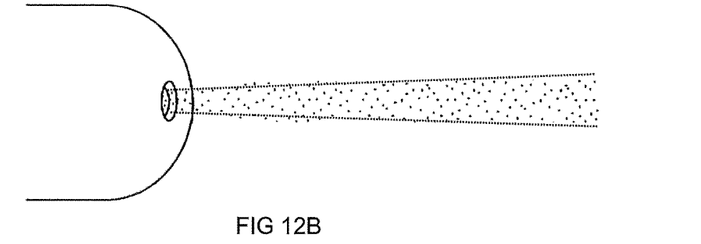
Figure 13:
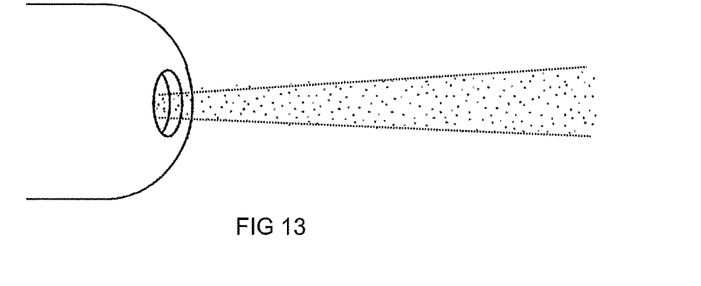
FIG. 13 shows the aerosolization plume that is generated by a nozzle with an aerosol exit orifice of 1200 µm in diameter at a compressed air pressure of 414 KPa (60 psi).

To evaluate the nature of a remarkable decrease in particle size with increasing aerosol exit orifice diameter 21, a series of photographs of aerosol plumes generated by these nozzles were taken while generating aerosols of water. Exemplary aerosol exit orifice diameter 21 variations are shown in FIGS. 11A and 11B with an aerosol exit orifice diameter 21 of 300 µm; FIGS. 12A and 12B with an aerosol exit orifice diameter 21 of 700 µm, and FIG. 13 with an aerosol exit orifice diameter 21 of 1200 µm. The fluid exit orifice diameter 23 in all cases was 250 µm and the distance 24 between the fluid exit orifice 6 and the entrance 53 to the aerosol exit channel 49, i.e. the length as the aerosolizing space 20 was 500 to 520 µm and the aerosol exit channel length 30 was 180-220 µm in all examples shown in FIGS. 11-13. The transformation of the nature of aerosol formation and emission from the nozzles is illustrated in FIG. 11A-B by comparing the plume formed outside a 300 µm diameter aerosol exit orifice 17 at 207 kPa (30 psi) and 1 ml/min and 414 kPa (60 psi) at 3 ml/min with the aerosol plume formed in the example shown in FIG. 12A-B within the aerosolizing space 20 exiting through a 700 µm diameter aerosol exit orifice 17 operated at 207 kPa (30 psi) and 1 ml/min and 414 kPa (60 psi) at 3 ml/min. The focused flow nature of the fluid as it exits the 300 µm diameter aerosol exit orifice 17 can be seen. This fluid stream from the 300 µm diameter aerosol exit orifice 17 undergoes Raleigh breakup to form a cone-shaped aerosol plume. In contrast, when a 700 µm diameter aerosol exit orifice 17 was used under the same compressed air pressures and fluid flow rates it can be seen that the aerosolization occurs prior to the aerosol exiting the aerosol exit orifice 17. It can also be seen that the plume is columnar shaped and that this columnar shaped plume exits the aerosol exit orifice 17 in a central core region of the nozzle surrounded by what appears to be a particle free zone between this central core region and the perimeter of the aerosol exit orifice 17. This particle-free gas surrounding the columnar aerosol plume can be seen in the examples shown in FIGS. 12A and 12B and even more clearly observed with the aerosol exit orifice 17 of 1200 µm in diameter (FIG. 13), operated at 414 kPa (60 psi) with an aerosolization rate of 3 ml/min. The transition from the focused flow nature of the aerosol produced to a substantially columnar aerosol plume (FIGS. 12A, 12B and 13) originating within the nozzle from the aerosolizing space 20 occurred for example at compressed air pressures above 276 kPa (40 psi) for a 400 µm diameter nozzle. This change in the nature of this aerosolization process was observed with all the larger nozzles and at all pressures tested. It was also observed that the aerosol free zone between the central columnar plume aerosol exit orifice increased with aerosol exit orifice diameter 21 and that the outer nozzle surface 18 of the aerosol exit orifice 17 was free from deposition of any fluid from the aerosol generated.

The performance of these nozzles was evaluated in conjunction with the aerosol processing system shown in FIG. 10 incorporated into a SUPRAER™ console. To evaluate the performance of these nozzles, aerosols were generated with aqueous solutions (w/v) of the excipient, polyvinylpyrrolidone (PVP) 8 kDa, 29 kDa, 40 kDa and 58 kDa as a protein, biologic or drug surrogate. The warmed compressed air and dilution air together with the infrared radiation were set to ensure complete evaporation of the water from the droplets generated, yielding dry aerosol particles. Measurements of particle size distributions at the output of the aerosol processing system were determined using a Marple-Miller cascade impactor. Measurements of the mass distributions were facilitated by the addition of 4% Allura Red AC (Sigma-Aldrich, USA) to the mass of PVP in the solution and analyzed spectrographically. The MMAD and the geometric standard deviation were determined from the cumulative log-probability plots. The outputs (delivered dose) of SUPRAER™ for nozzles were measured gravimetrically. The output was sampled using low resistance electrostatic filters at 44 l/min.

Figure 14:
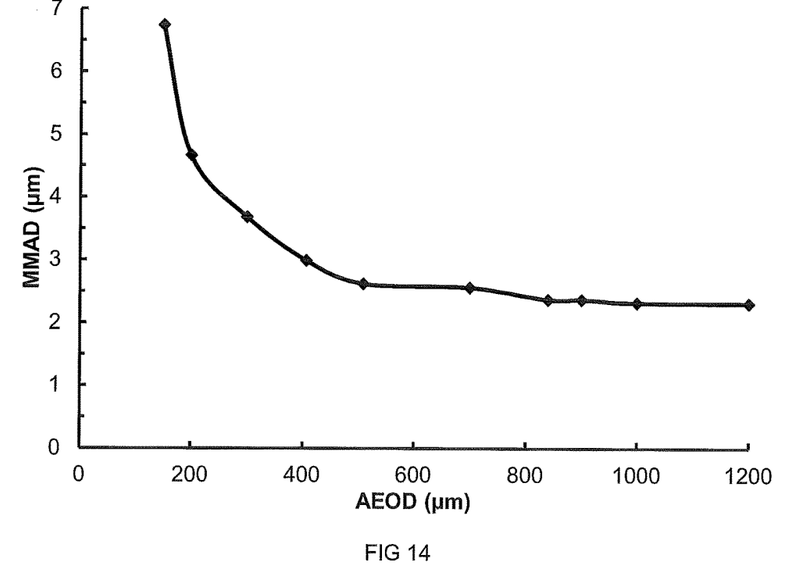
FIG. 14 shows a diagram demonstrating the influence of the aerosol exit orifice diameter (AEOD) on the mass median aerodynamic diameter (MMAD) of the aerosol particles in µm.

The effect of the aerosol exit orifice diameter 21 on particle size is shown in FIG. 14. At 207 kPa (30 psi) compressed air pressure at an aerosolizing rate of 1 ml/min and a concentration of 5% solution of 8 kDa PVP, the particle size of the output aerosol decreased with increases in the aerosol exit orifice diameter 21. The geometric standard deviation of the particle size distributions ranged from 1.7 to 2.15.

The diameter of the original droplets can be roughly estimated by multiplying the dry particle diameter by cube root of the ratio of water to PVP.

Figure 15:
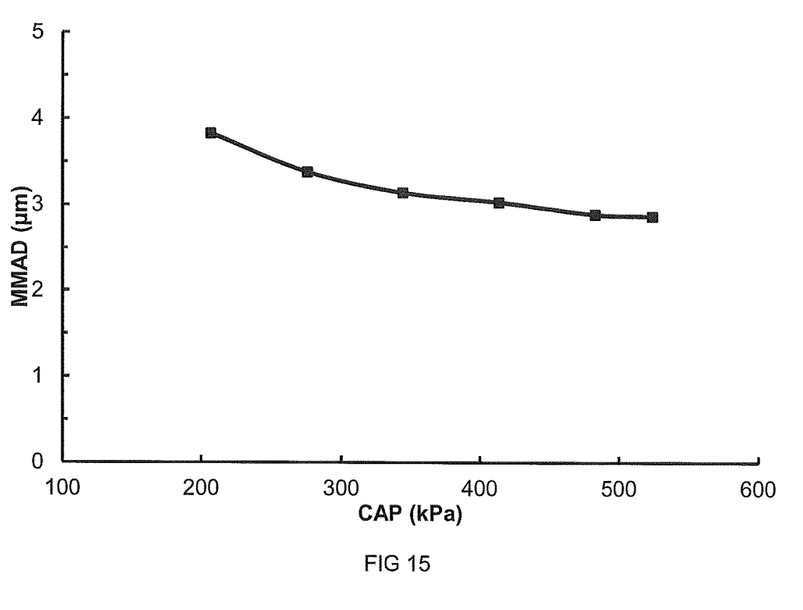
FIG. 15 shows a diagram demonstrating the influence of the compressed air pressure (CAP) in psi on the mass median aerodynamic diameter (MMAD) of the aerosol particles in µm.

The effect of compressed air pressure on particle size is shown in FIG. 15. The output particle size as given by the MMAD decreases with increasing compressed air pressure. The particles were generated at 1 ml/min with a nozzle having an aerosol exit orifice diameter 21 of 700 µm and using a 10% solution of 8 kDa PVP. Also, at 414 kPa (60 psi) aerosols of 40% 8 kDa PVP generated at 1 ml/min had a MMAD of 5.1 µm and geometric standard deviation of 2.0 was observed.

Figure 16:
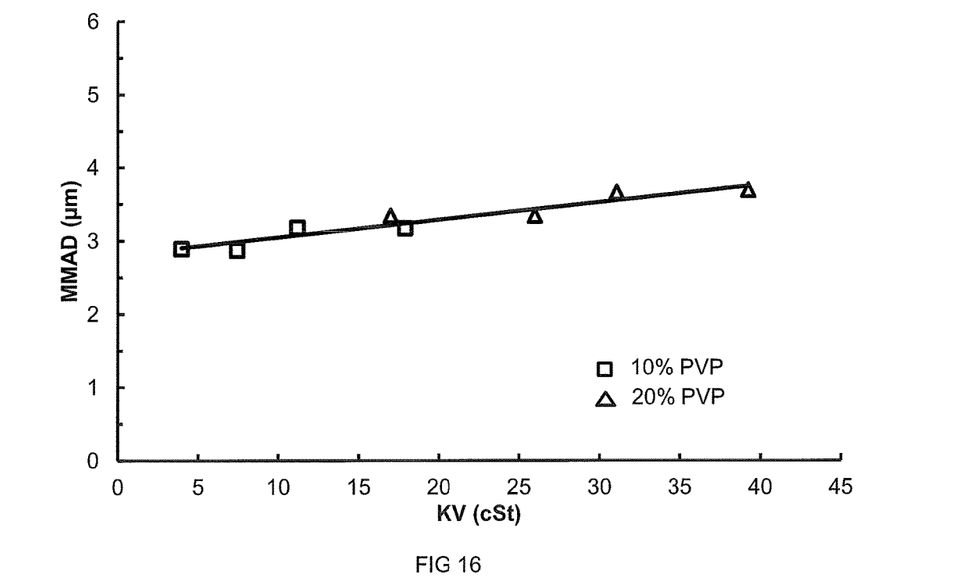
FIG. 16 shows a diagram demonstrating the influence of the kinematic viscosity KV of the fluid to be aerosolized in cSt on the mass median aerodynamic diameter (MMAD) of the aerosol particles in µm.

FIG. 16 demonstrates the effect of molecular weight/viscosity on the MMAD of the particles generated. The MMAD for 10% and 20% PVP solutions of 8 kDa, 29 kDa, 40 kDa and 58 kDa are shown. The particles generated from 20% PVP solutions, have a larger particle size than those generated from 10% PVP solutions. This FIG. 16 demonstrates that the particle size of the aerosols generated was relatively independent of the viscosity of the solution being aerosolized over the range of 4 to 40 cSt (~4 to 40 cP). This demonstrates an advantage of the incident invention, namely that the nozzle according to the incident invention delivers respirable aerosols over a wide range of viscosities at about the same particle size, i.e. is inviscid.

Aerosolization of solution concentrations of 5%, 10% 25% and 40% 8 kDa, PVP with the 700 μm diameter aerosol exit orifice 17 produced particles with MMAD's of 2, 3, 3.2, and 4.2 μm, respectively, with geometric standard deviations between 1.6 and 2.0.

The nozzles and aerosol processing system were used to generate aerosols from surfactant suspensions, including those containing phospholipids mimicking pulmonary surfactants. Aerosols were generated at 1 ml/min from a 10% suspension of surfactant liposomes having a viscosity of 34 cP and surface tension in the 22-24 mN/m range.

Figure 17:
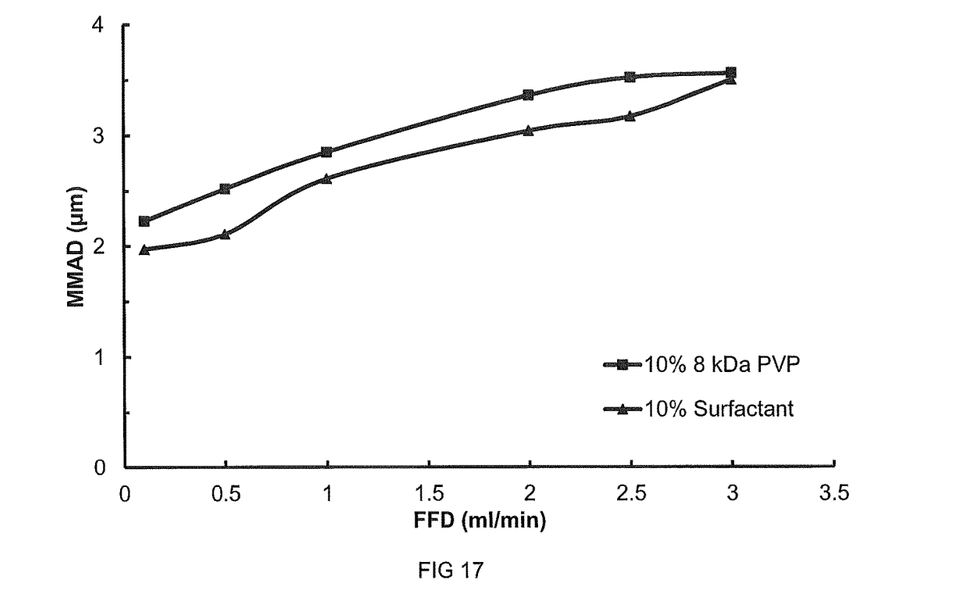
FIG. 17 shows a diagram demonstrating the influence of the fluid flow rate (FFD) of the fluid to be aerosolized in ml/min on the mass median aerodynamic diameter (MMAD) of the aerosol particles in μm for both PVP solutions and surfactant suspensions.

FIG. 17 demonstrates the effect of solution flow rate on the particle size for the 700 μm diameter aerosol exit orifice 17 at 414 kPa (60 psi). There was a modest linear in particle size with 10% 8 kDa PVP solution flow rates from 0.1 to 3 ml/min. When a 10% suspension of surfactant was aerosolized the particle size increased from 2.0 to 3.5 μm as the flow rate increased from 0.1 to 3 ml/min.

Table 1 demonstrates the mass output rate and efficiency for aerosols generated at increased flow rates for 20% 8 kDa PVP and 10% suspension of surfactant using a 500 and the 700 μm diameter aerosol exit orifices 17, respectively.

TABLE 1

The PVP mass output rate and efficiency for PVP and surfactant aerosols.

| Nozzle AEOD (μm) | Solution | Pressure (kPa) | Solute Flow Rate (ml/min) | Output (mg/mm) | Efficiency % |
|---|---|---|---|---|---|
| 500 | 20% 8 kDa PVP | 414 | 1 | 106 | 53% |
|  |  |  | 2 | 252 | 63% |
| 700 | 10% Surfactant | 207 | 1 | 53 | 53% |
|  |  | 414 | 1 | 46 | 46% |
|  |  |  | 2 | 92 | 46% |
|  |  |  | 3 | 126 | 42% |

Another 8.8% surfactant sample that had a viscosity of 57 cP measured using a capillary rheometer was tested. Using the 500 μm diameter nozzle at 414 kPa (60 psi) at an aerosolization rate of 2.5 ml/min and a MMAD of ~3.4 μm, an aerosol with a 1.7 geometric standard deviation was generated. A surfactant aerosol at a mass flow rate of 98 mg/min was collected.

Through the choice of aerosol exit orifice diameter 21, compressed air pressure, as well as solution concentration and solution flow rate, a selection of particles sizes and output rates over a wide range of concentrations and viscosities can be achieved. Of note, as the flow of fluid to be aerosolized is metered by a pump, the aerosol generation and output is constant. High concentrations (over 1 g/m$^3$) of pure fine particle aerosols can be delivered, thus potentially reducing treatment times from 20-100 min to 5-10 minutes as well as reducing exposure to excipients often used in dry powder inhalers. Such a device offers an attractive alternative to mesh-type and jet-type nebulizers for the generation and delivery of aerosols from relatively viscous solutions including biologics and surface-active agents. Such a device facilitates the efficient generation of aerosols of selectable particle size and concentration.

The medical applications of the incident invention include, but are not limited to, the aerosol delivery to the respiratory tract of surfactant, liposomal formulations, anti-infectives, mucolytics and gene transfer agents having viscous and surface properties within the ranges herein described.

The applications of this incident invention extend beyond the delivery of medications to the generation of fine particle aerosols for consumer and industrial applications where the fluid to be aerosolized has a viscosity above 10 cSt and or a low surface tension.

Further embodiments are given in the following paragraphs:

1. A nozzle 1 for generating from a fluid and a gas an aerosol comprising fluid particles, the nozzle 1 comprising:
    an aerosol exit orifice 17 extending to an outer nozzle surface 18, wherein the aerosol exit orifice 17 has an aerosol exit orifice diameter 21, a central axis 22 and has a circumferential edge 19 from which an aerosol exit channel 49 extends from the outer nozzle surface 18 toward an aerosolizing space 20 within the nozzle 1;
    a fluid exit orifice 6 that is aligned on the same central axis 22 as the aerosol exit orifice 17 and opens into the aerosolizing space 20 within the nozzle at a distance 24 from an entrance 53 to the aerosol exit channel 49, the aerosol exit orifice diameter 21 being at least 1.3 times larger than the fluid exit orifice diameter 23; and
    a converging annular pressurized gas channel 27 extending at an acute gas flow angle 61 with respect to the central axis 22 and having a pressurized gas exit 51 in close proximity to the fluid exit orifice 6 so as to intersect with fluid exiting from the fluid exit orifice 6.

2. The nozzle according to embodiment 1, wherein an aerosol exit channel length 30 of the aerosol exit channel 49 is less than the aerosol exit orifice diameter 21.

3. The nozzle according to embodiment 1 or embodiment 2, wherein the aerosol exit orifice diameter 21 is at least 1.5 times larger than the fluid exit orifice diameter 23.

4. The nozzle according to one of embodiments 1-3, wherein the distance 24 between the fluid exit orifice 6 and the entrance 53 to the aerosol exit channel 49 is greater than twice the fluid exit orifice diameter 23 and within a range between 100 μm and 2 mm.

5. The nozzle according to one of embodiments 1-4, wherein the converging annular pressurized gas channel 27 comprises a first partial annular channel 55 and a second partial annular channel 59, the first partial annular channel 55 has inner and outer walls formed by a conical wall 56 and an inner front insert wall 28 along which the pressurized gas flows with the acute gas flow angle 61 being determined by a conical wall angle 25 and a front insert wall angle 60 with respect to the central axis 22 in the area of the fluid exit orifice 6.

6. The nozzle according to embodiment 5, wherein the fluid supply channel 14 is provided within a cone-shaped fluid supply nozzle insert 4 forming the conical wall 56 that is the inner wall of the first partial annular channel 55, designed as a converging circumferential compressed gas channel that is axially centered in a cone-shaped hollow space 50 of the front insert 3 forming the inner front insert wall 28 that is the outer wall of the first partial annular channel 55.

7. The nozzle according to one of embodiments 1-6, wherein the outer nozzle surface 18 area is convex in the area of the aerosol exit orifice 17.

8. The nozzle according to one of embodiments 1-7, wherein the aerosolizing space 20 has the shape of a truncated cone having its small diameter at the entrance 53 to the aerosol exit channel 49.

9. The nozzle according to one of embodiments 1-8, wherein at least one of the inner front insert wall 28, outer cone-shaped fluid supply nozzle insert wall 29, aerosol exit channel 49, and the outer nozzle surface 18 area are hydrophobic, omniphobic, or lyophobic.

10. The nozzle according to one of embodiments 1-9, wherein the aerosol exit orifice 17 has an aerosol exit orifice diameter 21 between 400 μm and 1.2 mm.

11. The nozzle according to one of embodiments 1-10, wherein the acute gas flow angle 61 is between 10 and 30°.

12. The nozzle according to one of embodiments 1-11, wherein the first partial annular channel 55 diverges at an acute divergence angle 58 between 1 and 30°, the acute divergence angle 58 being the difference between the conical wall angle 25 and the front insert wall angle 60.

13. A method of generating an aerosol from a fluid and a gas by operating a nozzle comprising: an aerosol exit orifice 17 extending to an outer nozzle surface 18, wherein the aerosol exit orifice 17 has an aerosol exit orifice diameter 21, a central axis 22 and has a circumferential edge 19 from which an aerosol exit channel 49 extends from the outer nozzle surface 18 toward an aerosolizing space 20 within the nozzle 1; a fluid exit orifice 6 that is aligned on the same central axis 22 as the aerosol exit orifice 17 and opens into the aerosolizing space 20 within the nozzle at a distance 24 from an entrance 53 to the aerosol exit channel 49, the aerosol exit orifice diameter 21 being at least 1.3 times larger than the fluid exit orifice diameter 23; and a converging annular pressurized gas channel 27 extending at an acute gas flow angle 61 with respect to the central axis 22 and having a pressurized gas exit 51 in close proximity to the fluid exit orifice 6 so as to intersect with fluid exiting from the fluid exit orifice 6;

the method comprising:
aerosolizing a fluid with a viscosity exceeding 4 cSt delivering an inhalable medication; and
aerosolizing the fluid at a rate of more than 1 ml/minute, thereby delivering a medication at a mass flow rate of at least 30 mg/minute in form of the fluid particles having a mass median aerodynamic diameter (MMAD) of 6 μm or less.

14. The method according to embodiment 13, further comprising forming the aerosol within the aerosolizing space 20 and exiting this aerosolizing space 20 by the aerosol within a sheath of gas largely devoid of any aerosol particles.

15. The method according to embodiment 13 or claim 14, comprising aerosolizing a fluid with a viscosity between 4 and 40 cSt, wherein the mass median aerodynamic diameter (MMAD) of the particles generated in this viscosity range increases from 4 to 40 cSt by only up to 40%.

16. The method according to one of embodiments 13-15, comprising aerosolizing a fluid that is a surfactant suspension.

17. The method according to one of embodiments 13-16, comprising a step of drying the particles by evaporating fluid from the aerosol particles and increasing their concentration using a virtual impactor 46 to generate smaller dry powder particles in a reduced volume.

18. The method according to one of embodiments 13-17, comprising generating particle aerosols from solutions with viscosities greater than 40 cSt.

19. The method according to one of embodiments 13-18, comprising generating fine particle aerosols from aqueous suspensions with low surface tensions of between 2 and 72 mN/m.

20. The method according to one of embodiments 13-19, comprising impeding or preventing back flow of the aerosolizing fluid and potential nozzle malfunction by choosing an appropriate acute divergence angle 58 and by making the inner front insert wall 28 and the conical wall 56 of the first partial annular channel 55 hydrophobic, omniphobic or lyophobic.

LIST OF REFERENCE NUMERALS nozzle 1
nozzle holder 2
front insert 3
cone-shaped fluid supply nozzle insert 4
Luer connector 5
fluid exit orifice 6
knob 7
O-ring 8
barrel 9
channel 10
channel 11
channel 12
channel 13
fluid supply channel 14
gas entry port 15
pressurized gas supply channel 16
aerosol exit orifice 17
outer nozzle surface 18
circumferential edge 19
aerosolizing space 20
aerosol exit orifice diameter 21
central axis 22
fluid exit orifice diameter 23
distance 24
conical wall angle 25
pressure equalization chamber 26
converging annular pressurized gas channel 27
inner front insert wall 28
outer cone-shaped fluid supply nozzle insert wall 29
aerosol exit channel length 30
first hole 31
second hole 32
recess 33
recess 34
channel 35
flow distributor 36
port 37
counter-flow tube 38
output port 39
port 40
baffle 41
baffle 42
infrared source 43
quartz evaporation tube 44
acceleration nozzles 45
virtual impactor 46
exhaust ports 47
output cone 48
aerosol exit channel 49
cone-shaped hollow space 50
pressurized gas exit 51
deceleration nozzles 52
entrance 53 annular neck 54
first partial annular channel 55
conical wall 56
converging wall 57
acute divergence angle 58
second partial annular channel 59
front insert wall angle 60
acute gas flow angle 61
aerosolizing space wall 62

What is claimed is:

1. A nozzle for generating from a fluid and a gas an aerosol comprising fluid particles, the nozzle comprising:
    an aerosol exit orifice extending to an outer nozzle surface, wherein the aerosol exit orifice has an aerosol exit orifice diameter between 400 µm and 1.2 mm, a central axis and has a circumferential edge from which an aerosol exit channel extends from the outer nozzle surface toward an aerosolizing space within the nozzle;
    a fluid exit orifice that is aligned on the same central axis as the aerosol exit orifice and opens into the aerosolizing space within the nozzle at a distance between the fluid exit orifice and an entrance to the aerosol exit channel, the aerosol exit orifice diameter being at least 1.3 times larger than the fluid exit orifice diameter; and
    a converging annular pressurized gas channel extending at an acute gas flow angle with respect to the central axis and having a pressurized gas exit in close proximity to the fluid exit orifice so as to intersect with fluid exiting from the fluid exit orifice, wherein
    the converging annular pressurized gas channel comprises a first partial annular channel extending between an annular neck and the fluid exit orifice at the average acute gas flow angle of 10-30° with respect to the central axis;
    the first partial annular channel has inner and outer walls formed by a conical wall and an inner front insert wall along which the pressurized gas flows with the acute gas flow angle being determined by a conical wall angle and a front insert wall angle with respect to the central axis in an area of the fluid exit orifice, the inner front insert wall and the conical wall being hydrophobic, omniphobic or lyophobic;
    the first partial annular channel diverges at an acute divergence angle between 1 and 30°, the acute divergence angle being the difference between the conical wall angle and the front insert wall angle; and
    a fluid supply channel is provided within a cone-shaped fluid supply nozzle insert forming the conical wall that is the inner wall of the first partial annular channel, designed as a converging circumferential compressed gas channel that is axially centered in a cone-shaped hollow space of the front insert forming the inner front insert wall that is the outer wall of the first partial annular channel.

2. The nozzle according to claim 1, wherein an aerosol exit channel length of the aerosol exit channel is less than the aerosol exit orifice diameter.

3. The nozzle according to claim 1, wherein the aerosol exit orifice diameter is at least 1.5 times larger than the fluid exit orifice diameter.

4. The nozzle according to claim 1, wherein the distance between the fluid exit orifice and the entrance to the aerosol exit channel is greater than twice the fluid exit orifice diameter and within a range between 100 µm and 2 mm.

5. The nozzle according to claim 1, wherein the outer nozzle surface area is convex in an area of the aerosol exit orifice and this surface is hydrophobic, omniphobic, or lyophobic.

6. The nozzle according to claim 1, wherein the aerosolizing space has the shape of a truncated cone having its small diameter at the entrance to the aerosol exit channel.

7. The nozzle according to claim 1, wherein further at least one of an outer cone-shaped fluid supply nozzle insert wall, aerosol exit channel, and outer nozzle surface area are hydrophobic, omniphobic, or lyophobic.

8. A method of generating an aerosol from a fluid and a gas by operating a nozzle comprising: an aerosol exit orifice extending to an outer nozzle surface, wherein the aerosol exit orifice has an aerosol exit orifice diameter between 400 µm and 1.2 mm, a central axis- and has a circumferential edge from which an aerosol exit channel extends from the outer nozzle surface toward an aerosolizing space within the nozzle; a fluid exit orifice that is aligned on the same central axis as the aerosol exit orifice and opens into the aerosolizing space within the nozzle at a distance between the fluid exit orifice and an entrance to the aerosol exit channel, the aerosol exit orifice diameter being at least 1.3 times larger than the fluid exit orifice diameter; and a converging annular pressurized gas channel extending at an acute gas flow angle with respect to the central axis and having a pressurized gas exit in close proximity to the fluid exit orifice so as to intersect with fluid exiting from the fluid exit orifice; wherein the converging annular pressurized gas channel comprises a first partial annular channel extending between an annular neck and the fluid exit orifice at the average acute gas flow angle of 10-30° with respect to the central axis; the first partial annular channel has inner and outer walls formed by a conical wall and an inner front insert wall along which the pressurized gas flows with the acute gas flow angle being determined by a conical wall angle and a front insert wall angle with respect to the central axis in an area of the fluid exit orifice, the inner front insert wall and the conical wall being hydrophobic, omniphobic or lyophobic; the first partial annular channel diverges at an acute divergence angle between 1 and 30°, the acute divergence angle being the difference between the conical wall angle and the front insert wall angle; and a fluid supply channel is provided within a cone-shaped fluid supply nozzle insert forming the conical wall that is the inner wall of the first partial annular channel, designed as a converging circumferential compressed gas channel that is axially centered in a cone-shaped hollow space of the front insert forming the inner front insert wall that is the outer wall of the first partial annular channel;
    the method comprising:
    aerosolizing a fluid with a viscosity exceeding 4 cSt delivering an inhalable medication; and
    aerosolizing the fluid at a rate of more than 1 ml/minute, thereby delivering a medication at a mass flow rate of at least 30 mg/minute in form of the fluid particles having a mass median aerodynamic diameter (MMAD) of 6 µm or less.

9. The method according to claim 8, further comprising forming the aerosol within the aerosolizing space and exiting this aerosolizing space by the aerosol within a sheath of gas largely devoid of any aerosol particles.

10. The method according to claim 8, comprising aerosolizing a fluid with a viscosity between 4 and 40 cSt, wherein the mass median aerodynamic diameter (MMAD) of the particles generated in this viscosity range increases from 4 to 40 cSt by only up to 40%.

11. The method according to claim 8, comprising aerosolizing a fluid that is a surfactant suspension.

12. The method according to claim 8, comprising a step of drying the particles by evaporating fluid from the aerosol particles and increasing their concentration using a virtual impactor to generate smaller dry powder particles in a reduced volume.

13. The method according to claim 8, comprising generating particle aerosols from solutions with viscosities greater than 40 cSt.

14. The method according to claim 8, comprising generating fine particle aerosols from aqueous suspensions with low surface tensions of between 2 and 72 mN/m.

15. The method according to claim 8, comprising impeding or preventing back flow of the aerosolizing fluid and potential nozzle malfunction by choosing an acute divergence angle and by making the inner front insert wall and the conical wall of the first partial annular channel hydrophobic, omniphobic or lyophobic.

* * * * *

UNITED STATES PATENT AND TRADEMARK OFFICE
CERTIFICATE OF CORRECTION

| | | |
|---|---|---|
| PATENT NO. | : 9,573,147 B1 | Page 1 of 1 |
| APPLICATION NO. | : 15/130235 | |
| DATED | : February 21, 2017 | |
| INVENTOR(S) | : Donovan B. Yeates et al. | |

It is certified that error appears in the above-identified patent and that said Letters Patent is hereby corrected as shown below:

In the Specification

In Column 1, Line 9, the word "Exzampl" should be deleted.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*